United States Patent [19]

Ataka et al.

[11] Patent Number: 4,935,516

[45] Date of Patent: Jun. 19, 1990

[54] PROCESS FOR PREPARING 4-HYDROXYPYRIMIDINE

[75] Inventors: Kikuo Ataka; Kiyoshi Omori, both of Ube, Japan

[73] Assignee: UBE Industries, Ltd., Ube, Japan

[21] Appl. No.: 300,612

[22] Filed: Jan. 23, 1989

[30] Foreign Application Priority Data

Jan. 29, 1988 [JP] Japan .................. 63-17239

[51] Int. Cl.$^5$ .......................................... C07D 239/34
[52] U.S. Cl. .......................................... 544/319
[58] Field of Search .................................. 544/319

[56] References Cited

U.S. PATENT DOCUMENTS

| 3,047,462 | 7/1962 | Georges et al. | 167/65 |
| 3,895,112 | 7/1975 | De Angelis et al. | 424/251 |
| 3,950,525 | 4/1976 | De Angelis et al. | 424/251 |

FOREIGN PATENT DOCUMENTS 48-26020 8/1973 Japan .
48-39942 11/1973 Japan .
48-39943 11/1973 Japan .

OTHER PUBLICATIONS

Miller et al., s-Triazolopyrimidines. Part I. Synthesis as Potential Therapeutic Agents., J. Chemical Society, 5642-5659 (1963).
4-Methyl-6 Hydroxypyrimidine, Organic Synthesis, vol. 35, pp. 80-83 (1955).
Schroeder et al., Synthesis of Polyfluorinated Heterocycles by Indirect Fluorination with Silver Fluorides, II. (1962) Fluoropyrimidines, J. Org. Chem., vol. 27, p. 2580-2584.
Adams, Synthesis, pp. 286-288 (1974).
Bredereck et al., Eine Neue Pyrimidine-Synthese, A. Chem. Ber., vol. 90, pp. 942-952 (1957).
Heinrich Wamhoff, Adv. in Heterocyclic Chemistry, vol. 38, pp. 324-331 (1985).
Karl Gewald et al., Chem. Ber., vol. 101, pp. 1933-1939 (1968).
Synthesis, p. 595 (1982), Marsura et al.
G. Shaw et al., J. Chem. Soc., pp. 665-668 (1954).
Tetsuzo Kato et al., Chem. Pharm. Bull., vol. 24, pp. 303-309, (1976).

Alan R. Katritzky et al., Can. J. Chem., vol. 64, pp. 2087-2093 (1986).
Edward C. Taylor et al., J. Amer. Chem. Soc., vol. 82, pp. 3138-3141 (1960).

*Primary Examiner*—John M. Ford
*Attorney, Agent, or Firm*—Frishauf, Holtz, Goodman & Woodward

[57] ABSTRACT

A process for preparing a 4-hydroxypyrimidine of Formula III:

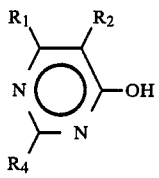

wherein $R_1$ and $R_2$ each represent a hydrogen atom, an alkyl group having 1 to 10 carbon atoms, a cycloalkyl group having 3 to 10 carbon atoms or an aralkyl group having 2 to 10 carbon atoms, and $R_4$ represents hydrogen an alkyl group having 1 to 10 carbon atoms, a cycloalkyl group having 3 to 10 carbon atoms, an aralkyl group having 7 to 10 carbon atoms or an aryl group having 6 to 10 carbon atoms, which comprises subjecting a 3-amino-2-unsaturated carboxylate of Formula I:

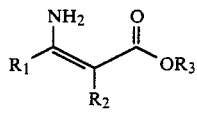

wherein $R_1$ and $R_2$ are as defined above and $R_3$ represents an alkyl group having 1 to 10 carbon atoms, a cycloalkyl group having 3 to 10 carbon atoms or an aralkyl group having 7 to 10 carbon atoms, and a carboxylic acid amide of Formula II:

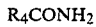

wherein $R_4$ is as defined above, to reaction with each other in the presence of a base.

29 Claims, No Drawings

PROCESS FOR PREPARING 4-HYDROXYPYRIMIDINE

BACKGROUND OF THE INVENTION

This invention relates to a process for preparing a 4-hydroxypyrimidine which is useful as a starting meterial for pharmaceuticals or agricultural chemicals.

The 4-hydroxypyrimidine is referred to as a 4-pyrimidone or a 4-pyrimidinol and preparation methods thereof have been described in detail, for example, in general remarks, D. J. Brown, "The chemistry of heterocyclic compounds, The Pyrimidines", 1962; "The chemistry of heterocyclic compounds, The Pyrimidines Supplement I", 1970; and "The chemistry of heterocyclic compounds, The Pyrimidines Supplement II", 1985 (all of them have been published by John Wiley & Son's Inc., New York).

In addition to the above described general remarks, a number of other preparation methods have been known as prior arts.

Typical preparation methods of a 4-hydroxypyrimidine which have conventionally been used in general and problems involved therein will be given below.

(i) A 4-hydroxypyrimidine is prepared according to a reaction between a β-ketoester and an amidine (reaction scheme 1, G. W. Miller and F. L. Rose, J. Chem. Soc., 5642–5659 (1963).

(reaction scheme 1)

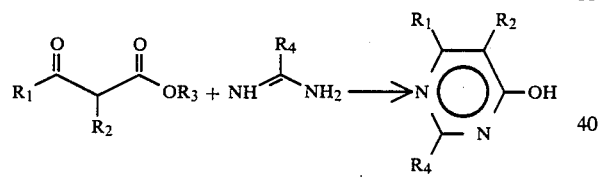

The reaction described above possibly gives a low yield in some cases depending on the kinds of the amidine employed (for example, formamidine). From industrial point of view, it is difficult to prepare the 4-hydroxypyrimidine at low cost since the amidin is expensive.

(ii) It is also possible to prepare a 4-hydroxypyrimidine by reacting a β-ketoester and thiourea with each other, followed by desulfurization of the resulting product by use of Raney nickel (reaction scheme 2, Organic Synthesis, 35, 80, 1955). This method gives a high yield in general, however, from an industrial point of view, it has a serious drawback to employ Raney nickel which is expensive and difficult to handle. Moreover, according to this method, it is impossible to introduce a substituent to the 2-position.

(reaction scheme 2)

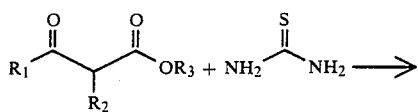

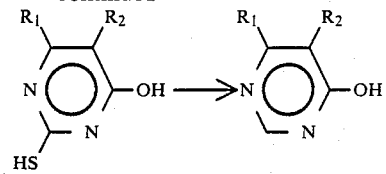

(iii) There can also be mentioned a patent that a 3-amino-2-unsubstituted carboxylic acid amide and an acid halide or a carboxylate are reacted with each other to prepare a 4-hydroxypyrimidine (reaction scheme 3; Japanese Patent Publication Nos. 26020/1973 and 39942/1973).

(reaction scheme 3)

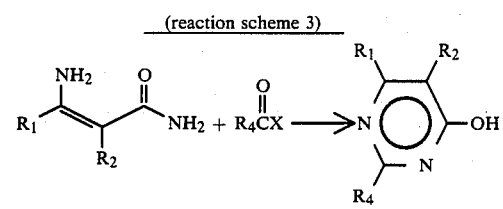

Although this reaction proceeds easily, the 3-amino-2-unsaturated carboxylic acid amide except for 3-aminocrotonic acid amide is extremely difficult to be prepared as a starting material and therefore this reaction has been utilized with difficulty in practice.

(iv) There can also be mentioned a process in which a pyrimidine having previously a substituent on the 4-position is subjected to reaction to prepare a 4-hydroxypyrimidine (reaction scheme 4, H. Schroeder, J. Org. Chem., 27, 2580, 1962).

(reaction scheme 4)

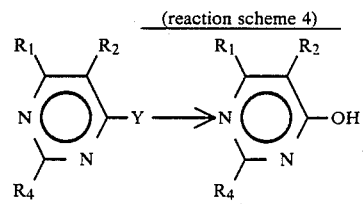

However, this process requires preparation of a pyrimidine having a substituent on the 4-position.

(v) A process has also been reported that a 4-hydroxypyrimidine is prepared from a β-ketoester, an ortho ester and ammonia (reaction schemes 5, V. D. Adams, Synthesis, 1974, [age 286).

(reaction scheme 5)

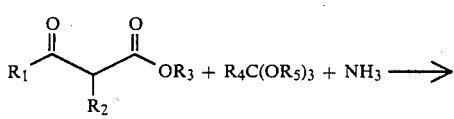

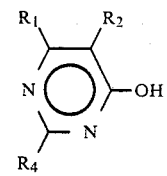

This process involves not only a problem of a high cost of the ortho ester but also a problem of an extremely low yield when an ortho formate having no substitutent at the 2-position is used.

(vi) There has also been reported a process in which a 4-hydroxypyrimidine is prepared from a β-ketoester, formamide and ammonia (reaction scheme 6, H. Brederck Ber., 90 942, 1957).

(reaction scheme 6)

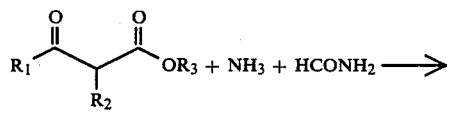

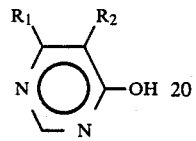

However, according to this process, 6-phenylpyrimidine only has been prepared at an extremely low yield.

As reactions similar to the present invention, there have been known a reaction in which a 4-hydroxyquinazoline is prepared from a 2-amino aromatic carboxylic acid such as anthoranilic acid or an ester thereof and formamide (U.S. Pat. No. 3,047,462) and a reaction in which a bicyclic 4-hydroxypyrimidine is prepared from a 2-aminocarboxylate having a hetero ring such as 3-aminopyrazole-4-carboxylate or 2-amonothiophene-3-carboxylate only through heating it with formamide (Advance in Heterocyclic Chemistry, 38 324, 1985). However, the compounds which have been actually used in the above reactions are those corresponding to a compound of Formula I described below in which $R_1$ and $R_2$ are connected to each other, and which are remarkably suitable for a cyclization reaction. When a compound in which $R_1$ and $R_2$ are not connected to each other is used, a desired product cannot be obtained even if the same reaction procedure as the above is carried out. U.S. Pat. No. 3,950,525 discloses that 6-phenyl-4-hydroxypyrimidine can be obtained from ethyl 2-aminocinnamate. However, this patent refers to a cinnamate derivative only but is silent about other derivatives. Further, the above reaction gives a low yield and takes a longer period for completion of the reaction, although a specific base such as potassium t-butoxide and a specific solvent such as dimethylsulfoxide are employed. Accordingly, it is difficult to apply this process for preparing other 4-hydroxypyrimidines in an industrial scale.

As described above, the conventional processes involve various problems therein in order to prepare a 4-hydroxypyrimidine industrially at a low cost.

In view from the circumstances described above, the present inventors have studied extensively a process for preparing a 4-hydroxypyrimidine which can be employed industrially, and completed the present invention.

The present invention provides a general method for preparing a 4-hydroxypyrimidine from a nono-cyclic 3-amino--2-unsaturated cabovxylate and a carboxylic acid amide, which can be easily employed in an industrial scale and resolves the problems involved in the conventional processes.

SUMMARY OF THE INVENTION

The 4-hydroxypyrimidine prepared according to the present invention is a compound which is referred to also as a 4-pyrimidone or a 4-pyrimidinol.

The present invention provides a process for preparing a 4-hydroxypyrimidine of Formula III:

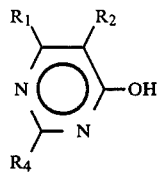

wherein $R_1$ and $R_2$ each represent a hydrogen atom, an alkyl group having 1 to 10 carbon atoms, a cycloalkyl group having 3 to 10 carbon atoms or an aralkyl group having 7 to 10 carbon atoms, and $R_4$ represents hydrogen an alkyl group having 1 to 10 carbon atoms, a cycloalkyl group having 3 to 10 carbon atoms, an aralkyl group having 7 to 10 carbon atoms or an aryl group having 6 to 10 carbon atoms, which comprises subjecting a 3-amino-2-unsaturated carboxylate of Formula I:

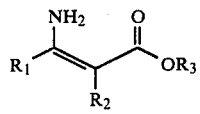

wherein $R_1$ and $R_2$ are as defined above and $R_3$ represents an alkyl group having 1 to 10 carbon a cycloalkyl group having 3 to 10 carbon atoms or an aralkyl group having 7 to 10 carbon atoms, and a carboxylic acid amide of Formula II:

wherein $R_4$ is as defined above, to reaction with each other in the presence of a base.

DESCRIPTION OF THE PREFERRED EMBODIMENTS

In the above described Formulas I, II and III, the alkyl group having 1 to 10 carbon atoms represented by $R_1$, $R_2$, $R_3$ or $R_4$ may include a straight or branched alkyl group as exemplified by a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, etc.

The cycloalkyl group having 3 to 10 carbon atoms represented by $R_1$, $R_2$, $R_3$ or $R_4$ may include a cyclopropyl group, a cyclobutyl group, a cyclopentyl group, a cyclohexyl group, etc.

The aryl group having 6 to 10 carbon atoms represented by $R_4$ may include, for example, a phenyl group, etc.

The aralkyl group having 7 to 10 carbon atoms represented by $R_1$, $R_2$, $R_3$ or $R_4$ may include, for example, a benzyl group, etc.

The 3-amino-2-unsaturated carboxylate of Formula I to be used as a starting material in the present invention can be easily prepared from a 3-ketocarboxylate and ammonia (S. A. Glickman, J. Am. Chem. Soc.,67 1017, 1946) and is exemplified by methyl 3-aminoacrylate, ethyl 3-aminoacrylate, butyl 3-aminoacrylate, methyl 3-aminocrotonate, ethyl 3-aminocrotonate, butyl 3-aminocrotonate, methyl 3-amino-2-pentenoate (pentenoic acid), ethyl 3-amino-2-pentenoate, butyl 3-amino-2-pentenoate, methyl 3-amino-4-phenylcrotonate, ethyl 3-amino-4-phenylcrotonate, methyl 3-aminomethacrylate, ethyl 3-aminomethacrylate, methyl 3-amino-2-methyl-2-pentenoate, ethyl 3-amino-2-methyl-2-pentenoate, methyl 3-amino-2-methylcrotonate, ethyl 3-amino-2-methylcrotonate, methyl 3-amino-2-benzylcrotonate, ethyl 3-amino-2-benzylcrotonate, methyl 3-amino-4-methyl-2-pentenoate, ethyl 3-amino-4-methyl-2-pentenoate, etc.

The carboxylic acid amide of Formula II to be used in the present invention may include, for example, formamide, acetamide, propionylamide, benzamide, etc.

As the base to be used in the present invention, an alkali metal alcoholate may preferably be used and there may be mentioned, for example, sodium methylate, sodium ethylate, soduim butylate, potassium methylate, potassium butylate, etc.

The present reaction proceeds without a solvent so long as the compounds of Formulas I and II are liquid at a reaction temperature, however, it is usually preferable to employ a solvent in the reaction. As the solvent, alcohols may give good results. Alcohols usable in the present invention may include methanol, ethanol, propanol, isopropanol, butanol, amyl alcohol, hexanol, etc. It is not necessary to employ the same alcohol as in the alcoholate (alkoxide) employed as the base.

The 4-hydroxypyrimidines obtainable in the present invention may include 4-hydroxypyrimidine, 6-methyl-4-hydroxypyrimidine, 2-methyl-4-hydroxypyrimidine, 6-ethyl-4-hydroxypyrimidine, 6-benzyl-4-hydroxypyrimidine, 2-phenyl-4-hydroxypyrimidine, 2,6-dimethyl-4-hydroxypyrimidine, 5,6-dimethyl-4-hydroxypyrimidine, 6-ethyl-5-methyl-4-hydroxypyrimidine, 6-ethyl-2-methyl-4-hydroxypyrimidine, 2-ethyl-6-methyl-4-hydroxypyrimidine, 6-methyl-2-phenyl-4-hydroxypyrimidine, 6-ethyl-2-phenyl-4-hydroxypyrimidine, 2,5,6-trimethyl-4-hydroxypyrimidine, 5-benzyl-6-methyl-4-hydroxypyrimidine, 5-methyl-4-hydroxypyrimidine, 6-isopropyl-4-hydroxy-pyrimidine, etc.

The carboxylic acid amide may be used in the present invention in an amount of 2-folds or more of the amount of the 3-amino-2-unsaturated carboxylate used. The larger amount of the carboxylic acid amide is used, the faster the reaction proceeds, however, it is preferable to use it in an amount of 2 to 10 folds from an economical view.

The base may be used in the present invention in an amount of 2-folds or more of the amount of the 3-amino-2-unsaturated carboxylate used and preferably in an amount of 2- to 5-folds.

The alcohol to be used as a solvent in the present invention may be a single alcohol or a mixed one and may be used in an amount of 2 to 20-folds of the amount of the 3-amino-2-unsaturated carboxylate used. If the starting materials are liquid at the reaction temperature, the reaction can proceed without a solvent as described above.

The reaction of the present invention can proceed at a temperature ranging from 20° to 200 ° C. and preferably from 90° to 130° C. The reaction can be completed within about 2 to 20 hours, although the reaction period depends upon the carboxylic acid amide, the alcoholate used, the concentration thereof and the reaction temperature.

The order of addition of the starting materials such as the carboxylic acid amide and 3-amino-2-unsaturated carboxylate is not particularly limited. However, it may be recommended to add a mixture or the carboxylic acid amide and 3-amino-2-unsaturated carboxylate into an alcoholic solution containing the base.

As an exemplified method for isolating the 4-hydroxypyrimidine formed in the reaction mixture, there may be mentioned a conventional method that after neutralization of the excess base with a mineral acid such as sulfuric acid or hydrochloric acid, an inorganic salts formed are removed, the resultant reaction solution (filtrate) is concentrated under a reduced pressure, and the resulting residue is subjected to distillation or recrystallization from an appropriate solvent.

According to the present process, the desired compound can be prepared from inexpensive starting materials at high yield with little by-product and with a simple procedure, which process can be said to be an extremely advantageous one from an industrial view.

EXAMPLE

The present invention will be described specifically below by referring to Examples, however, it is not limited to these Examples at all.

In the following examples, "%" means "% by weight", unless it is otherwise defined.

EXAMPLE 1

Synthesis of 6-ethyl-4-hydroxypyrimidine 12.9 g of methyl 3-amino-2-pentenoate, 45.1 g of formamide and 48.2 g of a 28 % methanolic solution of sodium methoxide are mixed and stirred under heating, and the methanol was distilled off until the internal temperature rose to 110° C. Subsequently, the reaction was carried out for 3 hours at 110° C. and after cooling, a quantitative analysis was carried out by high performance liquid (HPL) chromatography to reveal that 11.4 g of 6-ethyl-4-hydroxypyrimidine were formed (Yield: 91.9 mol %). After the reaction solution was neutralized with conc. sulfuric acid, the formed inorganic salt was removed off and the resulting filtrate was concentrated under a reduced pressure (5 mm Hg, 130° C., for 2 hours) and the residue obtained was subjected to recrystallization from acetone to give 10.1 g of a crystal of 6-ethyl-4-hydroxypyrimidine. m.p.: 131° to 134° C.; the conditions for HLP chromatography: column: ODS-80Tm; 4.6$\phi$×150 mm: detector: U.V. 254 nm; eluent: acetonitrile: water: triethylamine=500:500:1 adjusted to pH 6.5 with acetic acid; flow rate: 1 ml/min.; internal standard: α-picoline

EXAMPLE 2

Synthesis of 6-ethyl-4-hydroxypyrimidine

Into 600 ml of n-butanol were added 434.2 g of a 28% methanolic solution of sodium methoxide, and the solvent was distilled off until the internal temperature rose to 110° C. Subsequently, a mixture of 116.3 g of methyl 3-amino-2-pentenoate and 141.9 g of formamide was added dropwise over 1.5 hours, while the solvent was distilled off until the internal temperature rose to 110° C. The reaction mixture was further heated at 110° C. for 2 hours and then 20.3 g of formamide was further added. Thereafter the reaction mixture was heated for further 3 hours. After cooling, HPL chromatography analysis was carried out to reveal that 109 g of 6-ethyl-4-hydroxypyrimidine were formed (Yield: 97.8 mol %).

EXAMPLE 3

Synthesis of 6-methyl-4-hydroxypyrimidine

Into 133 ml of n-butanol were added 11.5 g of metal sodium, followed by heating to form sodium butoxide, which was then heated to 110° C. To the resulting solution, 50 ml of a n-butanolic solution containing 23.0 g of methyl 3-aminocrotonate and 31.5 g of formamide were added dropwise over 0.5 hour. The solvent was removed so that the internal temperature rose to 105° C. and at that temperature, heating was continued for further 3 hours. Then to the reaction mixture, 4.5 g of formamide were further added, followed by heating for further 3 hours. After cooling, HPL chromatography analysis was carried out to reveal that 20.3 g of 6-methyl-4-hydroxypyrimidine were formed (Yield: 92.3 mol %).

EXAMPLE 4

Synthesis of 6-ethyl-2-methyl-4-hydroxypyrimidine

Into 90 ml of n-butanol were added 72.4 g of a 28% methanolic solution of sodium methoxide, followed by heating and then the solvent was removed until the internal temperature rose to 105° C. Subsequently, 80 ml of a n-butanolic solution containing 19.4 g of methyl 3-amino-2-pentenoate and 22.2 g of acetamide were added dropwise over 1 hour, while the removal of the solvent was continued until the internal temperature rose to 110° C. At that temperature, heating was effected for further 2 hours. After cooling to a room temperature, HPL chromatography analysis was carried out to reveal that 18.1 g of 6-ethyl-2-methyl-4-hydroxypyrimidine were formed (Yield: 87.1 mol %). By treating the thus formed product in the same manner as in Example 1, a purified product having a melting point of 118.5° to 119° C. was obtained. Mass spectrum: M+138.

EXAMPLE 5

Synthesis of 6-ethyl-2-phenyl-4-hydroxypyrimidine

Into 60 ml of n-butanol were added 48.3 g of a 28% methanolic solution of sodium methoxide, followed by heating and then the solvent was removed until the internal temperature rose to 110° C. Subsequently, 60 ml of a n-butanolic solution containing 12.9 g of methyl 3-amino-2-pentenoate and 30.3 g of benzamide were added dropwise over 0.5 hour, while the removal of the solvent was continued until the internal temperature rose to 110° C. At that temperature, heating was continued for further 2 hours. After cooling to a room temperature, HPL chromatography analysis (under the same conditions as in Example 1) was carried out to reveal that 16.2 g of 6-ethyl-2-phenyl-4-hydroxypyrimidine were formed (Yield: 81.0 mol %). By treating the thus formed product in the same manner as in Example 1, a purified product having a melting point of 162° to 162.5° C. was obtained. Mass spectrum: M+200.

EXAMPLE 6

Synthesis of 5,6-dimethyl-4-hydroxypyrimidine

Into 45 ml of n-butanol were added 36.2 g of a 28% methanolic solution of sodium methoxide, followed by heating and then the solvent was removed until the internal temperature rose to 105° C. Subsequently, 30 ml of a n-butanolic solution containing 9.7 g of methyl 3-amino-2-methylcrotonate and 11.8 g of formamide were added dropwise over 0.5 hour, while the removal of the solvent was continued until the internal temperature rose to 110° C. At that temperature, heating was continued for further 4 hours. After cooling to a room temperature, HPL chromatography analysis (under the same conditions as in Example 1) was carried out to reveal that 7.8 g of 5,6-dimethyl-4-hydroxypyrimidine were formed (Yield: 83.8 mol %). By treating the thus formed product in the same manner as in Example 1, a purified product having a melting point of 206° to 207° C. was obtained. Mass spectrum: M+124.

EXAMPLE 7

Synthesis of 6-isopropyl-4-hydroxypyrimidine

Into 60 ml of n-butanol were added 48.3 g of a 28% methanolic solution of sodium methoxide, followed by heating and then the solvent was removed until the internal temperature rose to 110° C. Subsequently, 50 ml of a n-butanolic solution containing 12.9 g of methyl 3-amino-4-methyl-2-pentenoate and 45.0 g of formamide were added dropwise over 1 hour, while the removal of the solvent was continued until the internal temperature rose to 110° C. At that temperature, heating was continued for further 5 hours. After cooling to a room temperature, HPL chromatography analysis (under the same conditions as in Example 1) was carried out to reveal that 11.0 g of 6-isopropyl-4-hydroxypyrimidine were formed (Yield: 88.4 mol %). By treating the thus formed product in the same manner as in Example 1, a purified product having a melting point of 133.5° to 134.5° C. was obtained. Mass spectrum: M+138.

We claim:

1. A process for preparing a 4-hydroxypyrimidine of Formula III:

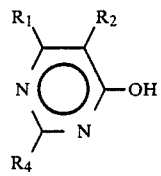

wherein $R_1$ and $R_2$ each represent a hydrogen atom, an alkyl group having 1 to 10 carbon atoms, a cycloalkyl group having 3 to 10 carbon atoms or an aralkyl group having 7 to 10 carbon atoms, and $R_4$ represents hydrogen an alkyl group having 1 to 10 carbon atoms, a cycloalkyl group having 3 to 10 carbon atoms, an aralkyl group having 7 to 10 carbon atoms or an aryl group having 6 to 10 carbon atoms, which comprises reacting a 3-amino-2-unsaturated carboxylate of Formula I:

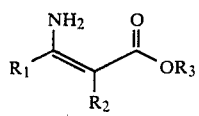

wherein $R_1$ and $R_2$ are as defined above and $R_3$ represents an alkyl group having 1 to 10 carbon atoms, a cycloalkyl group having 3 to 10 carbon atoms of an aralkyl group having 7 to 10 carbon atoms, with a carboxylic acid amide of Formula II:

wherein R₄ is as defined above, in the presence of a base.

2. The process according to claim 1, wherein said 3-amino-2-unsaturated carboxylate of Formula I is selected from the group consisting of methyl 3-aminoacrylate, ethyl 3-aminoacrylate, butyl 3-aminoacrylate, methyl 3-aminocrotonate, ethyl 3-aminocrotonate, butyl 3-aminocrotonate, methyl 3-amino-2-pentenoate (pentenoic acid), ethyl 3-amino-2-pentenoate, butyl 3-amino-2-pentenoate, methyl 3-amino-4-phenylcrotonate, ethyl 3-amino-4-phenylcrotonate, methyl 3-aminomethacrylate, ethyl 3-aminomethacrylate, methyl 3-amino-2-methyl-2-pentenoate, ethyl 3-amino-2-methyl-2-pentenoate, methyl 3-amino-2-methylcrotonate, ethyl 3-amino-2-methylcrotonate, methyl 3-amino-2-benzylcrotonate, ethyl 3-amino-2-benzylcrotonate, methyl 3-amino-4-methyl-2-pentenoate and ethyl 3-amino-4-methyl-2-pentenoate.

3. The process according to claim 2, wherein said 3-amino-2-unsaturated carboxylate of Formula I is selected from the group consisting of methyl 3-aminocrotonate, methyl 3-amino-2-pentenoate, methyl 3-amino-2-methylcrotonate and methyl 3-amino-4-methyl-2-pentenoate.

4. The process according to claim 1, wherein said carboxylic acid amide of Formula (II) is selected from the group consisting of formamide, acetamide, propionylamide and benzamide.

5. The process according to claim 1, wherein said base is an alkaline metal alcoholate.

6. The process according to claim 5, wherein said alkaline metal alcoholate is selected from the group consisting of sodium methylate, sodium ethylate, soduim butylate, potassium methylate and potassium butylate.

7. The process according to claim 1, wherein said reaction is carried out in a solvent.

8. The process according to claim 7, wherein said solvent is an alcohol.

9. The process according to claim 8, wherein said alcohol is selected from the group consisting of methanol, ethanol, propanol, isopropanol, butanol, amyl alcohol and hexanol.

10. The process according to claim 1, wherein said 4-hydroxy-pyrimidine is selected from the group consisting of 4-hydroxypyrimidine, 6-methyl-4-hydroxypyrimidine, 2-methyl-4-hydroxypyrimidine, 6-ethyl-4-hydroxypyrimidine, 6-benzyl-4-hydroxypyrimidine, 2-phenyl-4-hydroxypyrimidine, 2,6-dimethyl-4-hydroxypyrimidine, 5,6-dimethyl-4-hydroxypyrimidine, 6-ethyl-5-methyl-4-hydroxypyrimidine, 6-ethyl-2-methyl-4-hydroxypyrimidine, 2-ethyl-6-methyl-4-hydroxypyrimidine, 6-methyl-2-phenyl-4-hydroxypyrimidine, 6-ethyl-2-phenyl-4-hydroxypyrimidine, 2,5,6-trimethyl-4-hydroxypyrimidine, 5-benzyl-6-methyl-4-hydroxypyrimidine, 5-methyl-4-hydroxypyrimidine and 6-isopropyl-4-hydroxypyrimidine.

11. The process according to claim 10, wherein said 4-hydroxypyrimidine is selected from the group consisting of 6-methyl-4-hydroxypyrimidine, 6-ethyl-4-hydroxypyrimidine, 5,6-dimethyl-4-hydroxypyrimidine, 6-ethyl-2-methyl-4-hydroxypyrimidine and 6-isopropyl-4-hydroxypyrimidine.

12. The process according to claim 1, wherein said carboxylic acid amide is used in an amount of at least twice the amount of the 3-amino-2-unsaturated carboxylate used.

13. The process according to claim 1 wherein said base is used in an amount of at least twice the amount of the 3-amino-2-unsaturated carboxylate used.

14. The process according to claim 8, wherein said alcohol is used as a solvent in an amount of from 2 to 20 times the amount of the 3-amino-2-unsaturated carboxylate used.

15. The process according to claim 1, wherein said reaction is carried out at a temperature ranging from 20° to 200° C.

16. The process according to claim 1, wherein said reaction is carried out for 2 to 20 hours.

17. The process according to claim 2, wherein said carboxylic acid amide of Formula (II) is selected from the group consisting of formamide, acetamide, propionylamide and benzamide.

18. The process according to claim 3, wherein said carboxylic acid amide of Formula (II) is selected from the group consisting of formamide, acetamide, propionylamide and benzamide.

19. The process according to claim 17, wherein said base is an alkyline metal alcoholate and said reaction is carried out in an alcohol as a solvent.

20. The process according to claim 18, wherein said base is an alkaline metal alcoholate selected from the group consisting of sodium methylate, sodium ethylate, sodium butylate, potassium methylate and potassium butylate; and said reaction is carried out in an alcohol as a solvent, said alcohol being selected from the group consisting of methanol, ethanol, propanol, isopropanol, butanol, amyl alcohol and hexanol.

21. The process according to claim 1, wherein said compound of the Formula III is 6-ethyl-4-hydroxypyrimidine, said compound of the Formula I is methyl 3-amino-2-pentenoate and said compound of the Formula II is formamide.

22. The process according to claim 20, wherein said compound of the Formula III is 6-ethyl-4-hydroxypyrimidine, said compound of the Formula I is methyl 3-amino-2-pentenoate and said compound of the Formula II is formamide.

23. The process according to claim 22, wherein said formamide is in an amount 2 to 5 times that of said pentenoate.

24. The process according to claim 1, wherein said 3-amino-2-unsaturated carboxylate of Formula I is selected from the group consisting of methyl 3-aminoacrylate, ethyl 3-amino-acrylate, methyl 3-aminocrotonate, ethyl 3-aminocrotonate, methyl 3-amino-2-pentenoate, methyl 3-aminomethacrylate, ethyl 3-aminomethacrylate, methyl 3-amino-2-methyl-2-pentenoate, ethyl 3-amino-2-methyl-2-pentenoate, methyl 3-amino-2-methylcrotonate, ethyl 3-amino-2-methylcrotonate, methyl 3-amino-4-methyl-2-pentenoate and ethyl 3-amino-4-methyl-2-pentenoate;

wherein said carboxylic acid amide of Formula (II) is selected from the group consisting of formamide, acetamide, propyronlamide and benzamide;

wherein said base is selected from the group consisting of sodium methylate, sodium ethylate and sodium butylate; and wherein said reaction is carried out in an alcohol solvent selected from the group consisting of butanol, amyl alcohol and hexanol.

25. The process according to claim 24, wherein said carboxylic acid amide is used in an amount of 2 to 5 times the amount of said 3-amino-2-unsaturated carboxylate;

wherein said base is used in an amount of 2 to 5 times the amount of said 3-amino-2-unsaturated carboxylate;

wherein said alcohol used as a solvent is in an amount of 2 to 10 times the amount of said 3-amino-2-unsaturated carboxylate; and wherein said reaction is carried out at a temperature of from 100° to 200° C. for 2 to 10 hours.

26. The process according to claim 25, wherein said 3-amino-2-unsaturated carboxylate of Formula I is selected from the group consisting of methyl 3-amino-2-pentenoate, methyl 3-amino-2-methylcrotonate and methyl 3-amino-4-methyl-2-pentenoate.

27. The process according to claim 25, wherein said compound of the Formula III is 6-ethyl-4-hydroxypyrimidine, said compound of the Formula I is methyl 3-amino-2-pentenoate and said compound of the Formula II is formamide.

28. The process according to claim 25, wherein said 4-hydroxy-pyrimidine is selected from the group consisting of 4-hydroxypyrimidine, 6-methyl-4-hydroxypyrimidine, 2-methyl-4-hydroxypyrimidine, 6-ethyl-4-hydroxypyrimidine, 2,6-dimethyl-4-hydroxypyrimidine, 5,6-dimethyl-4-hydroxypyrimidine, 6-ethyl-5-methyl-4-hydroxypyrimidine, 6-ethyl-2-methyl-4-hydroxypyrimidine, 6-methyl-2-phenyl-4-hydroxypyrimidine, 6-ethyl-2-phenyl-4-hydroxypyrimidine, 2,5,6-trimethyl-4-hydroxypyrimidine, and 6-isopropyl-4-hydroxypyrimidine.

29. The process according to claim 25, wherein said 4-hydroxypyrimidine is selected from the group consisting of 6-ethyl-4-hydroxypyrimidine, 5,6-dimethyl-4-hydroxypyrimidine, 6-ethyl-2-methyl-4-hydroxypyrimidine and 6-isopropyl-4-hydroxypyrimidine.

* * * * *